(12) United States Patent
Dejongh et al.

(10) Patent No.: US 11,116,459 B2
(45) Date of Patent: Sep. 14, 2021

(54) PROTON IMAGING SYSTEM FOR OPTIMIZATION OF PROTON THERAPY

(71) Applicant: ProtonVDA LLC, Naperville, IL (US)

(72) Inventors: Don F. Dejongh, Batavia, IL (US); Victor Rykalin, Batavia, IL (US)

(73) Assignee: ProtonVDA LLC, Naperville, IL (US)

( * ) Notice: Subject to any disclaimer, the term of this patent is extended or adjusted under 35 U.S.C. 154(b) by 954 days.

(21) Appl. No.: 15/159,591

(22) Filed: May 19, 2016

(65) Prior Publication Data

US 2016/0338654 A1 Nov. 24, 2016

Related U.S. Application Data

(60) Provisional application No. 62/163,476, filed on May 19, 2015.

(51) Int. Cl.
| | |
|---|---|
| *A61B 6/00* | (2006.01) |
| *G01T 1/16* | (2006.01) |
| *G01T 1/29* | (2006.01) |
| *G01T 5/00* | (2006.01) |
| *A61N 5/10* | (2006.01) |

(52) U.S. Cl.
CPC .......... *A61B 6/4258* (2013.01); *A61B 6/4216* (2013.01); *A61B 6/5205* (2013.01); *A61B 6/582* (2013.01); *G01T 1/1603* (2013.01); *G01T 1/29* (2013.01); *G01T 5/00* (2013.01);
(Continued)

(58) Field of Classification Search
CPC .................................... G01T 1/29; G01T 5/00
See application file for complete search history.

(56) References Cited

U.S. PATENT DOCUMENTS

| | | | | |
|---|---|---|---|---|
| 4,829,185 A | * | 5/1989 | Kerff ....................... | C09B 11/00 250/361 R |
| 5,264,702 A | * | 11/1993 | Mihalczo .................. | G01T 3/06 250/390.01 |

(Continued)

FOREIGN PATENT DOCUMENTS

| | | |
|---|---|---|
| EP | 2746816 A1 | 6/2014 |
| WO | 2011100628 A2 | 8/2011 |

(Continued)

OTHER PUBLICATIONS

Coutrakon et al., "Design and construction of the 1st proton CT scanner," AIP Conference Proceedings, Jan. 1, 2013, pp. 327-331 (6 pages), New York, US.

(Continued)

*Primary Examiner* — Yi-Shan Yang
(74) *Attorney, Agent, or Firm* — Morrison & Foerster LLP

(57) ABSTRACT

A medical imaging system includes a first tracking detector and a second tracking detector. The tracking detectors are spaced to allow for an object to be present between the first tracking detector and the second tracking detector. The system also includes a residual range detector adjacent the first tracking detector. The residual range detector includes: (1) a scintillator material having a first surface at least partially covered with an anti-reflection material and a second surface facing the first tracking detector and (2) at least one photon detector coupled to the scintillator material at a third surface of the scintillator material different than the first surface and opposite the second surface.

17 Claims, 14 Drawing Sheets

(52) U.S. Cl.
CPC ............... *A61N 2005/1054* (2013.01); *A61N 2005/1087* (2013.01)

(56) References Cited

U.S. PATENT DOCUMENTS

| | | | | |
|---|---|---|---|---|
| 5,410,156 | A | | 4/1995 | Miller |
| RE36,201 | E | * | 4/1999 | Miller ................ G01N 23/09 |
| | | | | 250/390.04 |
| 6,078,052 | A | * | 6/2000 | DiFilippo ............... G01T 1/20 |
| | | | | 250/367 |
| 9,880,301 | B2 | * | 1/2018 | Schulte ............... G01N 23/04 |
| 2003/0147618 | A1 | * | 8/2003 | Guy .................. G02B 6/3849 |
| | | | | 385/139 |
| 2006/0108509 | A1 | * | 5/2006 | Frangioni ............ A61B 5/0059 |
| | | | | 250/208.1 |
| 2008/0011956 | A1 | * | 1/2008 | Burrell ................. G01T 1/202 |
| | | | | 250/367 |
| 2009/0266992 | A1 | * | 10/2009 | Beekman ............. G01T 1/1642 |
| | | | | 250/370.09 |
| 2012/0273665 | A1 | | 11/2012 | Schulte |
| 2013/0015352 | A1 | * | 1/2013 | Karonis ................ G01T 1/201 |
| | | | | 250/307 |
| 2015/0246244 | A1 | * | 9/2015 | Sossong ............... A61B 6/5235 |
| | | | | 600/427 |
| 2015/0297917 | A1 | * | 10/2015 | Beekman ............. A61N 5/1067 |
| | | | | 600/1 |
| 2015/0369744 | A1 | * | 12/2015 | Yang .................... B82Y 40/00 |
| | | | | 356/301 |

FOREIGN PATENT DOCUMENTS

| | | |
|---|---|---|
| WO | 2011162851 A2 | 12/2011 |
| WO | 2013055222 A1 | 4/2013 |
| WO | 2013186798 A2 | 12/2013 |

OTHER PUBLICATIONS

Hurley, et al., "Water-equivalent path length calibration of a prototype proton CT scanner," Medical Physics, AIP, May 1, 2012, pp. 2438-2446 (9 pages), vol. 39, No. 5, Melville, New York, US.

International Search Report and Written Opinion received for PCT Patent Application No. PCT/US2016/033313, dated Jul. 28, 2016, 22 pages.

Pemler, et al., "A detector system for proton radiography on the gantry of the Paul-Scherrer-Institute," Nuclear Instruments & Methods in Physics Research, Section A: Accelerators, Spectrometers, Detectors, and Associated Equipment, Aug. 11, 1999, pp. 483-495 (13 pages), vol. 432, No. 2-3, North Holland, NL.

Plautz et al., "200 MeV Proton Radiography Studies with a Hand Phantom Using a Prototype Proton CT Scanner," IEEE Transactions on Medical Imaging, IEEE Service Center, vol. 33, No. 4, Apr. 1, 2014, pp. 875-888 (7 pages), Piscataway, New Jersey, US.

Sadrozinski, et al., "Detector development for Proton Computed Tomography (pCT)," Nuclear Science Symposium and Medical Imaging Conference (NSS/MIC), 2011 IEEE, IEEE, Oct. 23, 2011, pp. 4457-4461 (5 pages).

Uzunyan et al., "A New Proton CT Scanner," 23rd Conference on Application of Accelerators in Research and Industry, CAARI 2014, Aug. 29, 2014, 6 pages, San Antonio, Texas. Retrieved from: http://arxiv.org/pdf/1409.0049v2.pdf (retrieved on Jul. 18, 2016).

Notice of Acceptance dated Nov. 18, 2020 for AU Application No. 2016264493, three pages.

European Office Action dated Sep. 4, 2020, for EP Application No. 16728773.9, ten pages.

Notice of Reasons for Rejection, dated Sep. 4, 2020, for JP Application No. 2017-560812, with English translation, 9 pages.

Notification of the First Office Action, dated Apr. 2, 2020, for CN Application No. 201680029239.9, with English translation, 35 pages.

Coutrakon, G. et al. (Mar. 30, 2014). "A New Proton CT Detector," 23rd Conference on Application of Accelerators in Research and Industry, NL, Elsevier, URL, https://arxiv.org/abs/1409.0049, six pages.

Penfold, Scott Nicholas. (Sep. 21, 2011). "Image reconstruction and Monte Carlo simulations in the development of proton computed tomography for applications in proton radiation therapy," University of Wollongong Thesis Collection, AU, University of Wollongong, URL, http://ro.uow.edu.au/theses/3305. (submit in 2 parts).

Presti, D. Lo et al. (Mar. 9, 2014). "Development of a Real-Time, Large Area, High Spatial Resolution Particle Tracker Based on Scintillating Fibers," Advances in High Energy Physics, Great Britain, Hindawi Publishing Corporation, vol. 2014, Article ID 692908, pp. 1-13.

Notice of Reasons for Rejection, dated May 25, 2020, for JP Application No. 2017-560812, with English translation,15 pages.

Examination report dated Aug. 10, 2020 for AU Application No. 2016264493, four pages.

Notification of the Second Office Action, dated Feb. 5, 2021, for CN Application No. 201680029239.9, with English translation, 27 pages.

Notice of Final Rejection, dated Mar. 23, 2021, for JP Application No. 2017-560812, with English translation, 3 pages.

* cited by examiner

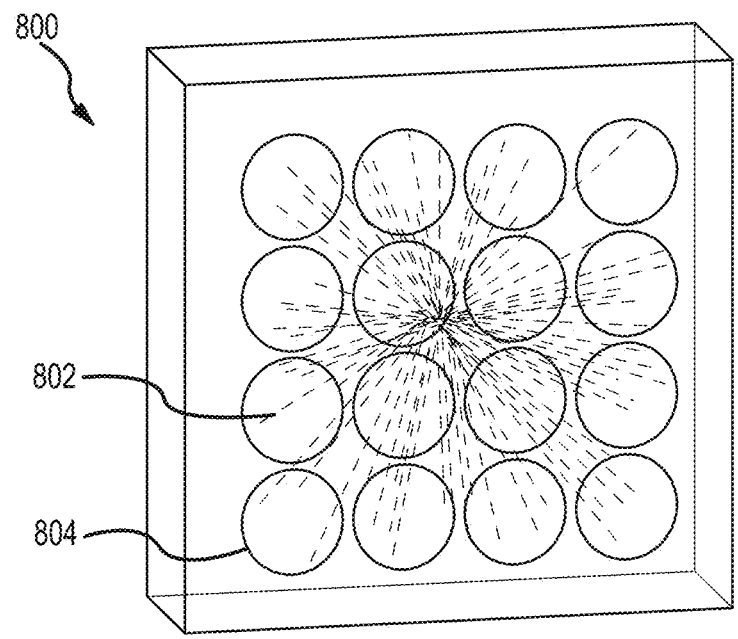
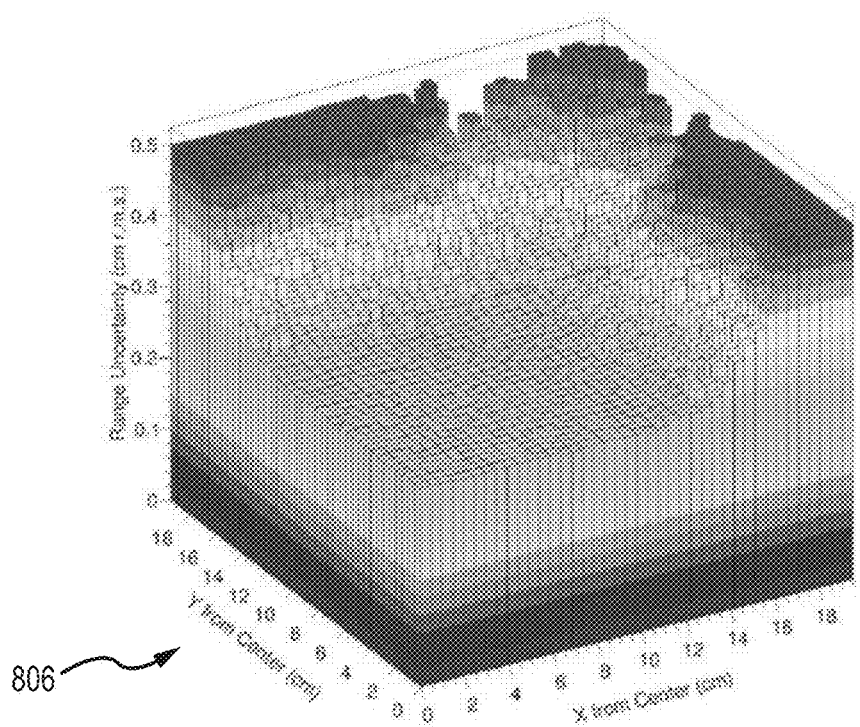
FIG.8

PROTON IMAGING SYSTEM FOR OPTIMIZATION OF PROTON THERAPY

CROSS-REFERENCE TO RELATED APPLICATION

This application claims priority to U.S. Prov. Pat. App. Ser. No. 62/163,476, filed May 19, 2015, and entitled A PROTON IMAGING SYSTEM FOR OPTIMIZATION OF PROTON THERAPY, the entirety of which is hereby incorporated in its entirety by reference.

STATEMENT REGARDING FEDERALLY SPONSORED RESEARCH OR DEVELOPMENT

This invention was made with government support from the National Cancer Institute of the National Institutes of Health under Award Number R43CA203499. The government has certain rights in the invention.

BACKGROUND

The Bragg peak phenomena enables particles such as protons or ions to precisely target tumors for radiation therapy, while healthy tissues receive a minimal dose when compared with x-ray therapy systems. Proton radiation therapy however requires precise patient alignment, and also adjustment of initial proton energy so that the maximum dose corresponding to the Bragg peak is deposited in intended tissues. In order to adjust the range of a proton beam, so that the maximum dose corresponding to the Bragg peak is deposited in intended tissues, treatment planning may require three-dimensional map of a particular patient in terms of relative stopping power, or the energy loss of the proton beam in a material relative to that of water.

SUMMARY

One embodiment of a medical imaging system includes a first tracking detector and a second tracking detector. The first tracking detector is spaced from the second tracking detector to allow for an object to be present between the first tracking detector and the second tracking detector. A residual range detector is adjacent the first tracking detector. The residual range detector includes: (1) a scintillator material having a first surface at least partially covered with an anti-reflection material and a second surface facing the first tracking detector; and (2) at least one photon detector coupled to the scintillator material at a third surface of the scintillator material different than the first surface and opposite the second surface.

BRIEF DESCRIPTION OF THE DRAWINGS

FIG. 8 shows a second detector placement simulation according to the disclosure.

DETAILED DESCRIPTION

Figure 1:
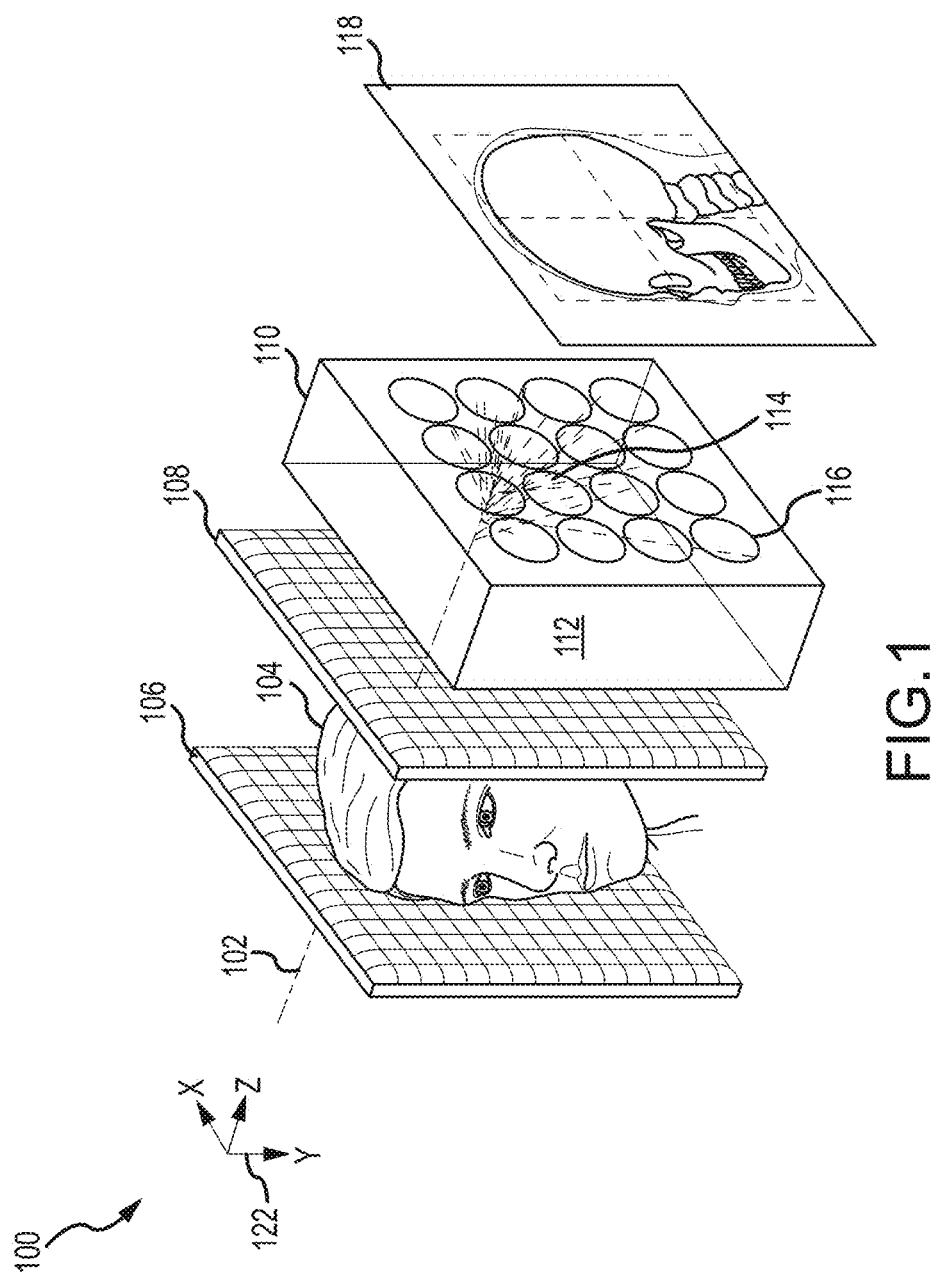
FIG. 1 shows a proton radiography system according to the disclosure.

Embodiments of a medical imaging system, such as a proton radiography system or a proton tomography system, are described. In some embodiments, a proton radiography system includes a first tracking detector, a second tracking detector, and a residual range detector. In this embodiment, the first and second tracking detectors use a fiber bundling architecture that, among other things, significantly improves proton transverse position resolution while reducing the complexity of the proton radiography system. The residual range detector uses a light collection architecture that, among other things significantly improves proton residual range resolution while simplifying the overall residual range detector design.

Some variations of the fiber bundling architecture used in the first and second tracking detectors utilize a planar substrate and include at least two layers of scintillating fibers on each side of the substrate that extend along particular directions. More specifically, each one of the fibers on one side of the substrate extends along a direction that is perpendicular to a direction of each one of the fibers on the opposite side of the substrate.

Some variations of the bundling architecture also use (a) an adjacent layer bundling scheme and/or (b) a lateral strip-based bundling scheme. In the adjacent layer bundling scheme, one fiber from each layer on one side of the substrate are bundled together to form a fiber doublet. In the lateral strip-based bundling scheme, groups of fibers or fiber doublets on each side of the substrate are segmented or partitioned into strips or sections of a particular number of fiber or fiber doublets (e.g., a strip of ten fibers or ten fiber doublets). In some examples, particular fibers or fiber doublets (e.g., the fourth fiber or the fourth fiber doublet) of each strip are bundled together and coupled to a same anode of a particular multi-anode light detector (or other type of photon detector).

Many benefits and advantages flow from the fiber bundling architecture of the present technology. For example, the number of light detectors and electronics channels required to resolve proton transverse position are substantially reduced, while at the same time proton transverse position resolution approaches 0.3 mm or better, when compared to conventional proton radiography systems. By extension, the described fiber bundling architecture addresses many of the issues associated with conventional proton radiography systems, which are also bulky and expensive both in terms of component and data processing costs.

Regarding the light collection architecture, the residual range detector includes a scintillator material that, in some examples, is a bulk piece of material. The residual range detector also includes at least one light detector coupled to the scintillator material at a surface of the scintillator material. If the at least one light detector comprises a plurality of light detectors, they may be arranged to exhibit a unit cell pattern selected from, for example, square, rectangular and polygonal. Additionally, in some examples, an anti-reflective material (e.g., a thin film, other coating, or cover) is present on at least one surface (or multiple surfaces) of the scintillator material.

Many benefits and advantages flow from the light collection architecture of the present disclosure. For example, both the amount of time required to collect scintillation light and scintillation light collection efficiency are substantially improved, while at the same time residual range resolution approaches 3.0 mm or better per proton, when compared to conventional proton radiography systems. By extension, the disclosed light collection architecture addresses many of the issues associated with typical proton radiography systems, which also suffer from proton residual range resolution error that propagates through to map reconstruction during the treatment planning process.

Exemplary embodiments of a medical imaging system that utilize one or more of the above features are described in further detail below. While protons are used an example particle for use with the system described below, other particles (e.g., ions of other elements, including helium ions, lithium ions, beryllium ions, carbon ions, boron ions, deuterons) could also be used. Additionally, while a proton radiograph system is described below, the present technology could also be used in other medical imaging systems, such as a proton tomography system.

FIG. 1 depicts system 100, which is an embodiment of a proton radiography system according to the present technology. In some examples, a pencil beam 102 (alternatively, a broad beam could also be used with variations of the present technology) of protons (although other particles, such as heavy ions, could also be used) is generated or extracted from a source (see FIG. 2) and scanned across a field by a scanning element (see FIG. 2). For example, pencil beam 102 is scanned across a region of interest of object 104, which is a human head in FIG. 1. The position of pencil beam 102 as it enters object 104 can be determined based on data from tracking detector 106 that generates photons at locations where protons traverse tracking detector 106, as described in more detail below. Similarly, the position of pencil beam 102 as it exits object 104 can be determined using data from tracking detector 108. Note that tracking detectors 106 and 108 are spaced apart to allow object 104 to be positioned between them. In some embodiments, only one tracking detector is needed or two or more tracking detectors are used on one or both sides of object 104. Potential architectures for tracking detectors 106 and 108 are described in more detail below.

Residual range detector 110 is positioned adjacent tracking detector 108. Residual range detector 110 includes scintillator material 112 (represented in FIG. 1 by a box). In one example, the scintillator material may be one sold by Eljen Corporation. As a proton of pencil beam 102 enters scintillator material 112 through the surface facing tracking detector 108, the proton generates photons 114 (represented by dotted lines in FIG. 1) as the protons loses energy from interacting with scintillator material 112. These photons can then be collected by photon detectors (FIGS. 2 and 5) coupled to scintillator material 112 on the surface of scintillator material 112 that is opposite the surface facing tracking detector 108. The coupling of the photon detectors is depicted in FIG. 1 by circles 116. The signal generated by the photon detectors is proportional to a residual energy of a proton as it entered scintillator material 112. This information combined with the initial energy of the proton and the location of the proton as it entered and exited object 104, along with similar information for many additional protons, can be used to generate image 118 of object 104. By using multiple proton energies and/or protons at different angles (e.g., 100 different angles) in a proton tomography system using the present technology, 3D images can also be produced.

Figure 2:
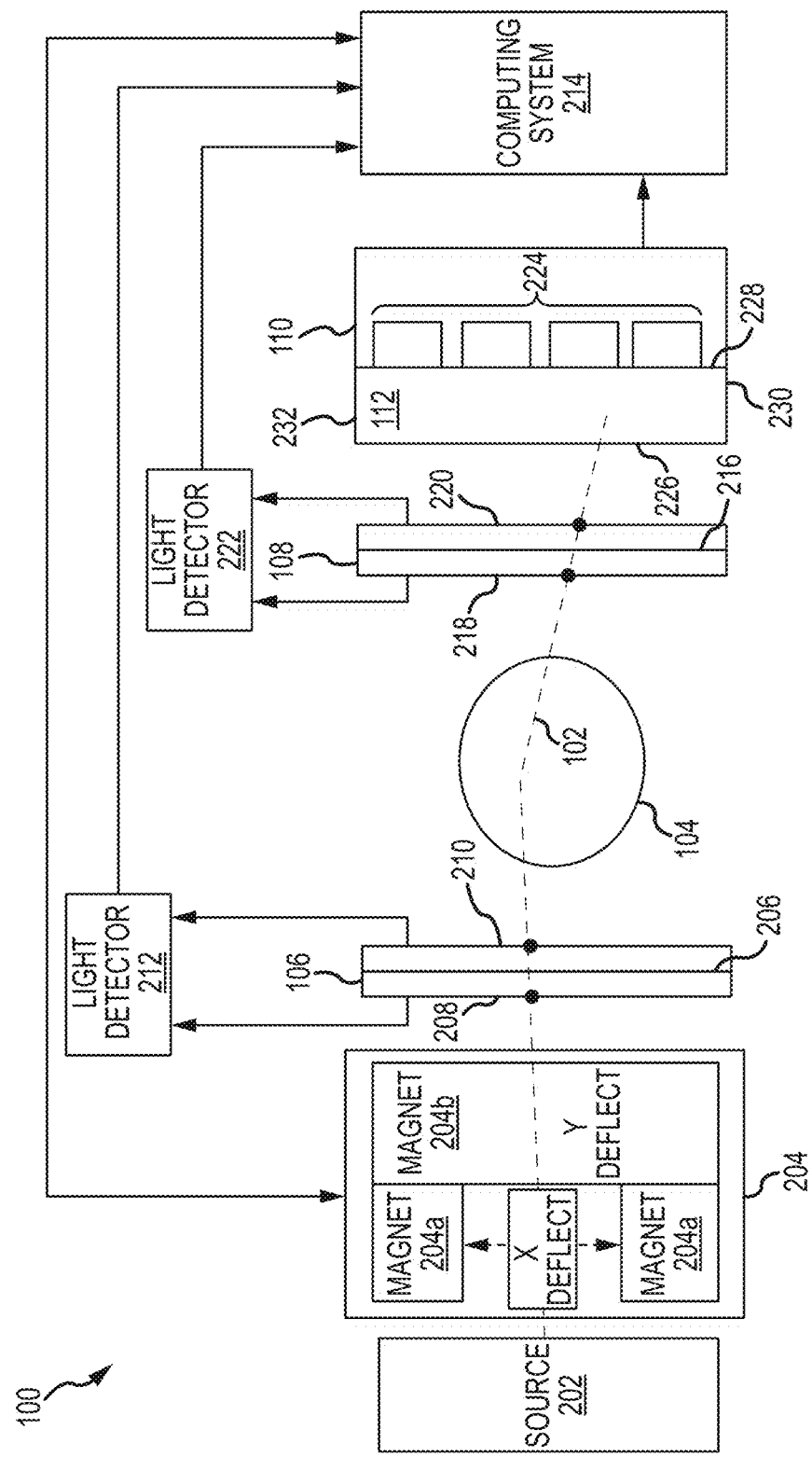
FIG. 2 shows the system of FIG. 1 in more detail and in block diagram form.
Figure 3:
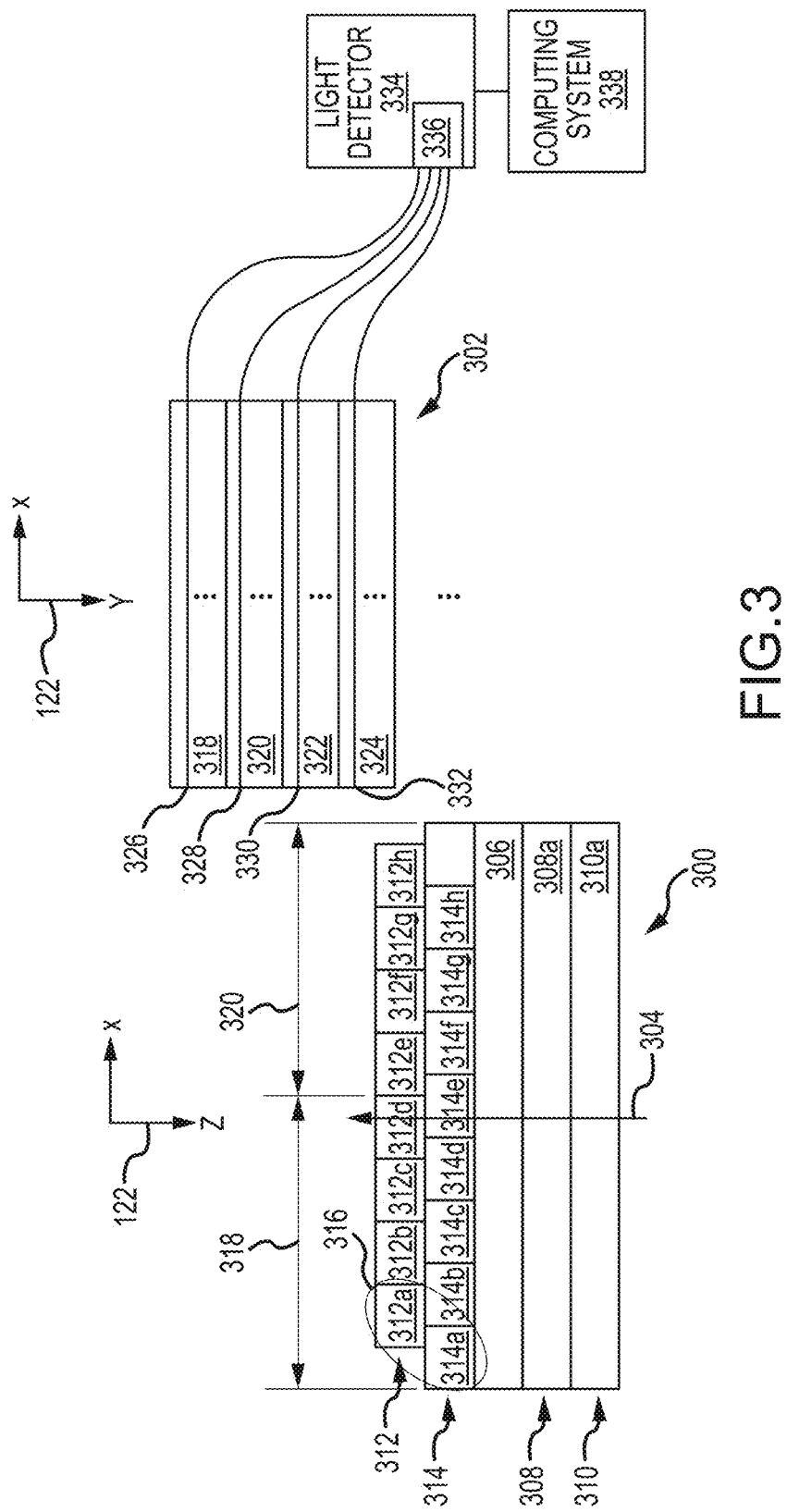
FIG. 3 shows multiple views of a tracking detector of the system of FIG. 1.

Note that reference axes 122 show that pencil beam 102 is traveling along the z-axis and tracking detectors 106 and 108 are perpendicular to the z-axis. FIGS. 2 and 3 described below will be described with respect to the same reference axes.

FIG. 2 depicts system 100 of FIG. 1 with additional detail and from a different perspective, as indicated by reference axes 122. With reference to FIG. 2, system 100 includes source 202 that generates or extracts pencil beam 102. Scanning element 204 is used to steer pencil beam 102 and includes scanning magnets 204a and 204b. Scanning magnets 204a scan the pencil beam 102 in x-directions as defined with respect to reference axes 122, and scanning magnets 204b (the second of which is hidden in the perspective of FIG. 2) scan pencil beam 102 in y-directions as defined with respect to respect to reference axes 122. In general, scanning element 106 is programmable such that pencil beam 102 is scan-able across the entirety of the field in any pattern, and, as determined by source 202, at any initial energy at any point in time. In this example, source 202 is capable of controlling or varying the initial energy of the protons of pencil beam 102. During a scan, the extent of the field is in general limited by the planar dimensions of first tracking detector 106, second tracking detector 108, or residual range detector 114 of system 100. Example field areas include 10×10 cm$^2$ to 38.4×38.4 cm$^2$.

By using a different initial energy at different transverse positions of the tracking detectors and the object being imaged, the depth of the residual range detector can be kept small. For example, the initial energies can be chosen to keep the residual range between 0 and 10 cm across the field to be imaged regardless of the thickness or density of the object along a particular path. The more range in initial energy that is possible, smaller residual range detectors may be possible.

In some examples of an architecture for tracking detector 106, as protons of pencil beam 102 traverse first tracking detector 106, the protons interact with fibers either side of substrate 206. Specifically, each side of substrate 206 includes, for example, two layers of fibers, i.e., fibers 208 on one side and fibers 210 on the opposite side of substrate 206. Fibers 208 and 210 may be scintillating fibers so that when a proton impinges a fiber, the scintillating properties of the fiber will cause one or more photons to be generated. These photons are captured by light detector 212, which generates an electrical signal based on the detected photons. The electrical signal is transmitted to computing system 214. By knowing the location and orientation of fibers 208 and 210 that produced photons, the location of the proton that traversed tracking detector 106 may be determined by computing system 214. Additionally, computing system 214 may also use data from scanning element 204 to determine or verify the location where a proton passed through tracking detector 106. Once the location is known the initial directional vector of pencil beam 102 can also be determined based on the focal point of source 202.

In some examples, fibers 208 are oriented perpendicular to fibers 210. If light detector 212 indicates that a proton passed through one fiber of fibers 208 and one fiber of fibers 210 and computing system 214 knows the location of these two fibers, computing system 214 can determine that the X-Y coordinate on tracking detector 106 where the proton traversed tracking detector 106 is at the intersection of the two fibers. Additionally, if fibers of fibers 208 or fibers of fibers 210 are connected together to reduce the number of detectors needed in light detector 212, then the estimated expected position of pencil beam 102 based on data from or instructions sent to scanning element 204 may be used in determining the X-Y coordinate where the proton traversed tracking detector 106, as described in more detail below with respect to FIG. 3.

As protons of pencil beam 102 traverse object 104, protons may be scattered, as is depicted in FIG. 2 as an exaggerated change in direction of pencil beam 102 in object 104. After the protons exit object 104, the exit location where protons traverse tracking detector 108 can be determined in a similar manner as described above with respect to tracking detector 106. Similar to tracking detector 106, tracking detector 108 includes fibers on substrate 216. Specifically, each side of substrate 216 includes, for example, two layers of fibers, i.e., fibers 218 on one side and fibers 220 on the other side of substrate 216. Fibers 218 and 220 may be scintillating fibers so that when a proton impinges a fiber, the scintillating properties of the fiber will cause one or more photons to be generated. These photons may be captured by light detector 222, which may generate an electrical signal based on the detected photons. The electrical signal is transmitted to computing system 214. By knowing the location and orientation of fibers 218 and 220 that produced photons, the location of the proton that traversed first tracking detector 108 may be determined by computing system 214. Additionally, computing system 214 may also use information from scanning element 204 to determine or verify the location on tracking detector 108 where a proton passed through tracking detector 108.

In some examples, fibers 218 are oriented perpendicular to fibers 220. If light detector 222 indicates that a proton passed through one fiber of fibers 218 and one fiber of fibers 220 and computing system 214 knows the location of these two fibers, computing system 214 can determine that the X-Y coordinate on tracking detector 108 where the proton traversed tracking detector 108 is at the intersection of the two fibers. Additionally, if fibers of fibers 218 or fibers of fibers 220 are connected together to reduce the number of detectors needed in light detector 222, then the estimated or expected position of pencil beam 102 based on data from or instruction sent to scanning element 204 may be used in determining the X-Y coordinate on tracking detector 108 where the proton traversed tracking detector 108, as described in more detail below with respect to FIG. 3.

While an exemplary architecture of a tracking detector has been described, other architectures are possible. For example, if fibers are rigid enough, the fibers could be bonded together to avoid using a substrate. As another example, with respect to tracking detector 106, fibers 208 and 210 could be placed on the same side of substrate 206 or fibers 208 and 210 could be placed on separate substrates that are placed next to each other.

As protons of pencil beam 102 enter residual range detector 110, they impinge scintillator material 112 and generate photons that are collected by photon detectors 224 (while four photon detectors are depicted in FIG. 2, system 100 includes sixteen photon detectors as indicated by the circles representing the photon detectors couplings to scintillator material 112 in FIG. 1). Photon detectors 224 are, for example, photomultiplier tubes or other similar devices. Photon detectors 224 generate electrical signals based on the number of photons collected and generate electrical signals that are provided to computing system 214, which may calculate values such as total energy. Based on the electrical signals, and potentially other information (such as the X-Y coordinate of where a proton exited object 104 and traversed tracking detector 108), computing system 214 may determine a residual energy for a proton of pencil beam 102 that entered scintillator material 112 after exiting object 104.

Protons enter scintillator material 112 via surface 226. Generated photons are collected by photon detectors 224 as the photon exit surface 228 of scintillator material 112. The dimensions of scintillator material 112 may be selected to ensure that protons stop in scintillator material 112 as opposed to passing through scintillator material 112. This ensures that protons of pencil beam 102 generate a large number of scintillation photons within a few nanoseconds. Surface 226, surface 230, surface 232, and/or the other two surfaces of scintillator material 112 not depicted in FIG. 2 are, in some examples, covered (e.g., deposited, coated, or arranged next) with an anti-reflective or photon absorbing material. For example, the walls of scintillator material 112 are painted black. The anti-reflective material ensures that mainly direct photons that have not scattered off the walls of scintillator material 112 are collected at photon detectors 224. The anti-reflective material may include different materials on different surfaces of scintillator material 112. In one example, the anti-reflective material may be Eljen Corporation EJ510B black paint. The anti-reflective material may absorb 90% or more of the photons that contact the material. The anti-reflective material adds to the high speed operation of system 100.

The use of multiple photon detectors also provides the potential to obtain additional position data for the location that a proton exited object 104. For example, with reference to FIG. 1, if photon detectors are coupled to scintillator materials 112 as indicated by circles 116 (sixteen total), the photon detector nearest where the photon entered scintillator material 112 should produce the strongest signal. If the position of the photon detector that produces the strongest signal does not correlate with the position indicated by the signals generated from tracking detector 108 and light detector 222, then an event that should be rejected may exist, such as inelastic scatter.

FIG. 3 depicts two cross-sections of a tracking detector that may be used to implement tracking detectors 106 and 108 (FIGS. 1 and 2). Cross-section 300 depicts tracking detector along the plane parallel to the z-axis and x-axis, as depicted in reference axes 122. Cross-section 302 depicts the same tracking detector along the plane parallel to the y-axis and x-axis, as depicted in reference axes 122, which is also perpendicular to the plane of cross-section 300. Additionally, cross-section 302 is zoomed-out as compared to cross-section 300. In cross-section 300, the direction of protons is along the z-axis as depicted by path 304. In cross-section 302, the direction of protons is coming out of the figure.

As depicted in cross-section 300, the tracking detector includes a substrate 306 having two layers of fibers, 308 and 310, respectively, on one side and two layers of fibers, 312 and 314, respectively on the other side. Layers of fibers 308 and 310 are laid out perpendicular to layers of fibers 312 and 314. Only one fiber of layer of fibers 308 and one fiber of layer of fibers 310 are visible because the other fibers are blocked from view. Layer of fibers 312 includes fibers 312a-312h and layer of fibers 314 includes fibers 314a-314h. As depicted in FIG. 3, the layers of fibers on each side of the substrate may be offset from each other so that fibers of one layer (e.g., layer 312) are positioned between two fibers in the adjacent layer (e.g., layer 314). In other words, the fibers in one layer may be offset from the other layer by about one half the width of a single fiber. In this layout, protons that go through the interface between two fibers in one layer, should also go through the middle of the fiber in the next layer, which results in higher efficiency. Other architectures could have additional layers of fibers or only a single layer of fibers.

Fibers of adjacent layers can be bundled together so they connect to a single light detector channel. For example, with reference to FIG. 3, fibers 312a and 314a can be bundled together into fiber doublet 316 so fibers 312a and 314a connect to a single channel of the light detector. In some cases, bundling occurs by combining the ends of fibers 312a and 314a in parallel so that the outputs of fibers 312a and 314a can be detected together.

Multiple fibers or fiber doublets may be organized in logical strips. For example, if fibers 312a-312d are respectively bundled with fibers 314a-314d to form four fiber doublets, the four fiber doublets may be treated as strip 318. Similarly, if fibers 312e-312h are respectively bundled with fibers 314e-314h to form four fiber doublets, the four fiber doublets may be treated as strip 320. A strip may include more fibers or fiber doublets, such as 64 fibers or fiber doublets.

To further reduce the number of channels required in a light detector, similarly positioned fibers or fiber doublets in strips on a side of substrate 306 may be bundled together and connected to a single channel of the light detector. In this case, the location of the fiber or fiber doublet that generated photons within the strips in combination with the expected location of the pencil beam can be used to located the position of the pencil beam accurately to within, for example, 0.3 mm when using 1 mm² fibers. For example, the expected location of the pencil beam can be used to determine the expect strip where the proton will be and the fiber or fiber doublet that produces photons can be used to identify the location within the strip of the proton.

The two types of bundling described above (i.e., bundling adjacent fibers of different layers and bundling fibers or fiber doublets of different strips) can be used together or separately in different variations of the present technology.

Cross-section 302 depicts strips 318, 320, 322, and 324, which of which includes a plurality of fiber doublets. For example, strip 318 includes four fiber doublets made of fibers 312a-312d and fibers 314a-314d (e.g., fiber doublet 316), as described above. Similarly, strip 318 include fiber doublet 326, strip 320 include fiber doublet 328, strip 322 includes fiber doublet 330, and strip 324 includes fiver doublet 332. Because fiber doublets 318, 320, 322, and 324 are located at the same positions within strips 318, 320, 322, and 324, the outputs of these fiber doublets may be bundled together and connected to light detector 334 via a single channel (i.e., channel 336). Light detector 334 includes several channels (not shown) that are each connected to a group of fiber doublets that have the same position in the strips of the tracking detector. Light detector 334 provides electrical signals to computing system 338 representative of photons generated in the fibers of the tracking detector as received by the channels (e.g., channel 336) of light detector 334.

While an exemplary architecture of a tracking detector has been described in FIG. 3, the same bundling architecture could be used in other configurations of tracking detectors. For example, with respect to the tracking detector of FIG. 3, if fibers are rigid enough, fiber layers 308, 310, 312, and 314 could be bonded together to avoid using a substrate. As another example, fiber layers 308 and 310 could be placed on the same side of substrate 306 as fiber layers 312 and 314. In another example, fiber layers 308 and 310 could be placed on a separate substrate than fiber layers 312 and 314 and the two substrates could be placed next to each other.

Figure 4:
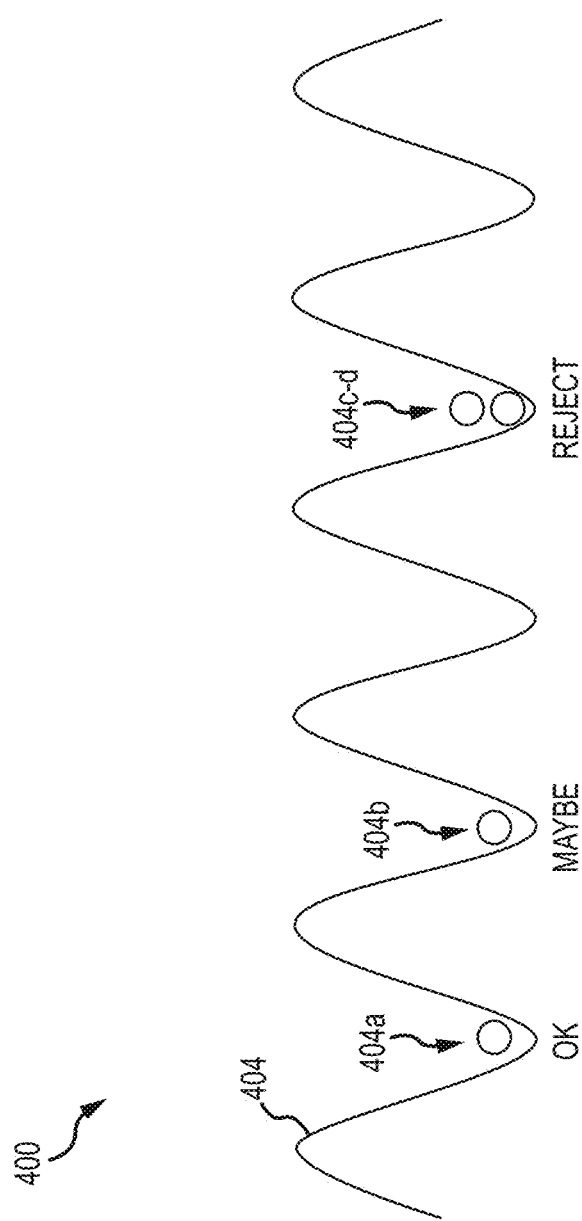
FIG. 4 shows a proton bunch train according to the disclosure.

FIG. 4 illustrates a proton bunch train 400 whereby individual protons 402a-d are superimposed on a sinusoid 404 that represents an RF (Radio Frequency) accelerating field. In some examples, bunches with more than one proton (e.g., protons 402c-d) are rejected for image analysis or map reconstruction but will still contribute to radiation dose. Bunches in adjacent cycles (e.g., protons 402a-b) may be used for image analysis or map reconstruction if the residual range detector recovers in time to detect protons that impinge in immediately subsequent cycles.

Figure 5:
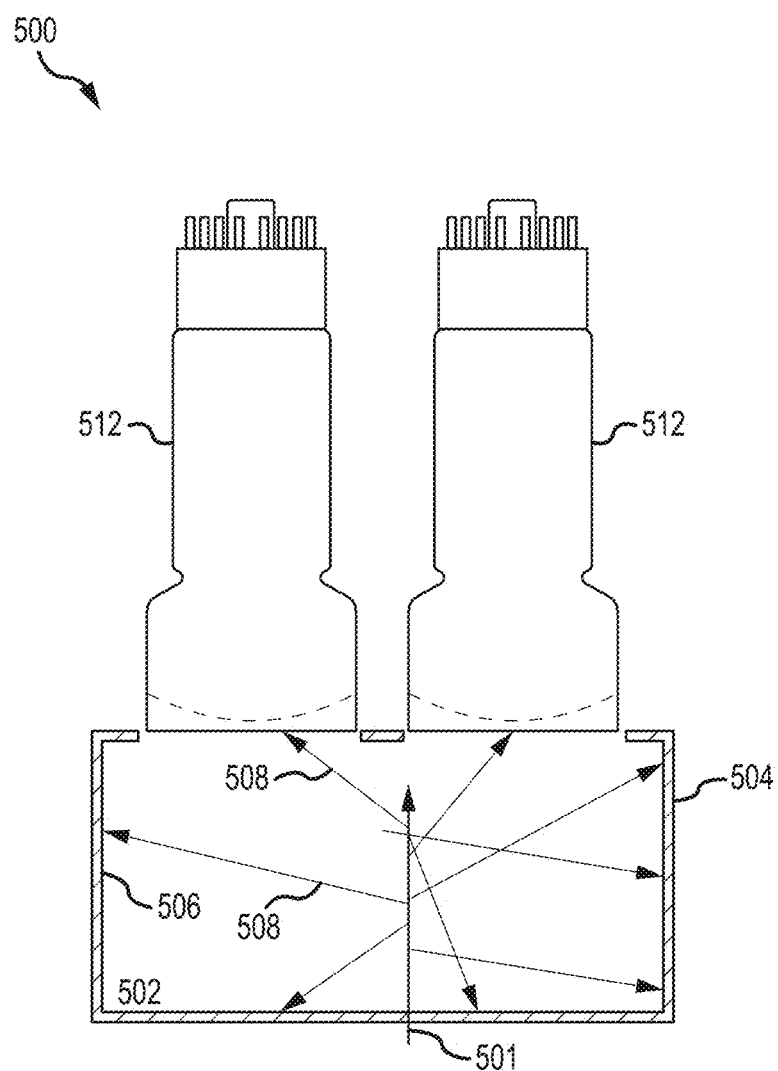
FIG. 5 shows a residual range detector of the system of FIG. 1.

FIG. 5 depicts residual range detector 500 that could be used to implement residual range detector 110 of system 100 of FIGS. 1-2. Residual range detector 500 includes scintillator material 502, which, in some examples, is a bulk scintillator material. Scintillator material 502 may be contained within an enclosure 504 that provides for an anti-reflective surface for photons generated in scintillator material 502. Alternatively, scintillator material 502 may also have an anti-reflective coating (e.g., a thin film) deposited on the surfaces (e.g., surface 506) of scintillator material 502. Photons 508 are generated in scintillator material 502 by a proton entering scintillator material 508 along path 510. Only direct photons are collected by the photon detectors 512, this enhances light collection efficient and speed.

Figure 6:
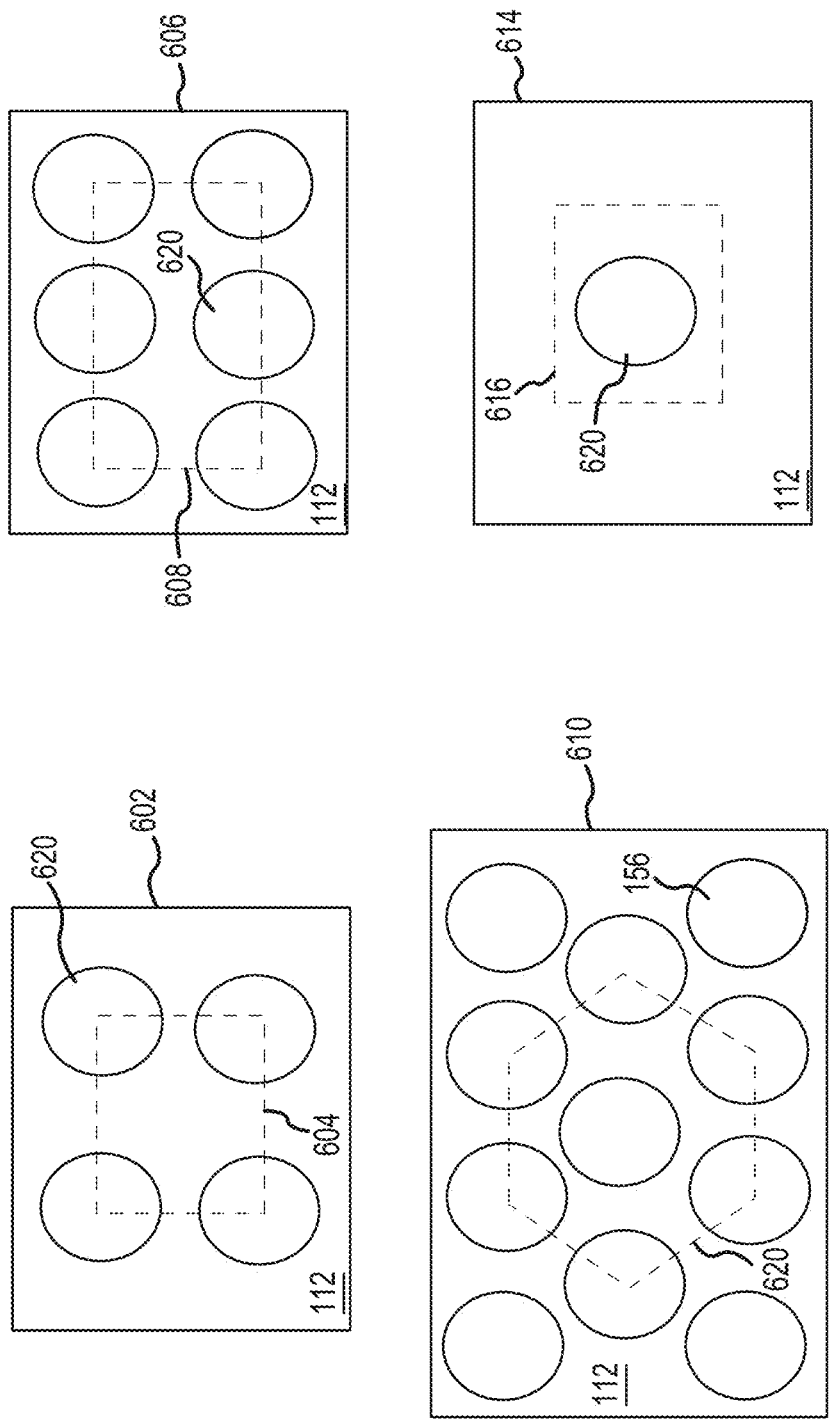
FIG. 6 shows multiple light detector patterns according to the disclosure.

FIG. 6 illustrates multiple unit cell patterns of photon detectors coupled to the scintillator material 112 of FIG. 2. The coupling locations of the photon detectors are indicated by circles 620. Pattern in example 602 is a square unit cell pattern 604. Pattern in example 606 is a rectangular unit cell pattern 608. Pattern in example 610 is a polygonal unit cell pattern 612. Pattern in example 614 is a square pattern 616 where only a single detector is present. Trade-offs govern which pattern is selected, e.g., polygonal unit cell pattern 612 might be selected if very high precision is required and cost and bulkiness is not an issue.

Figure 7:
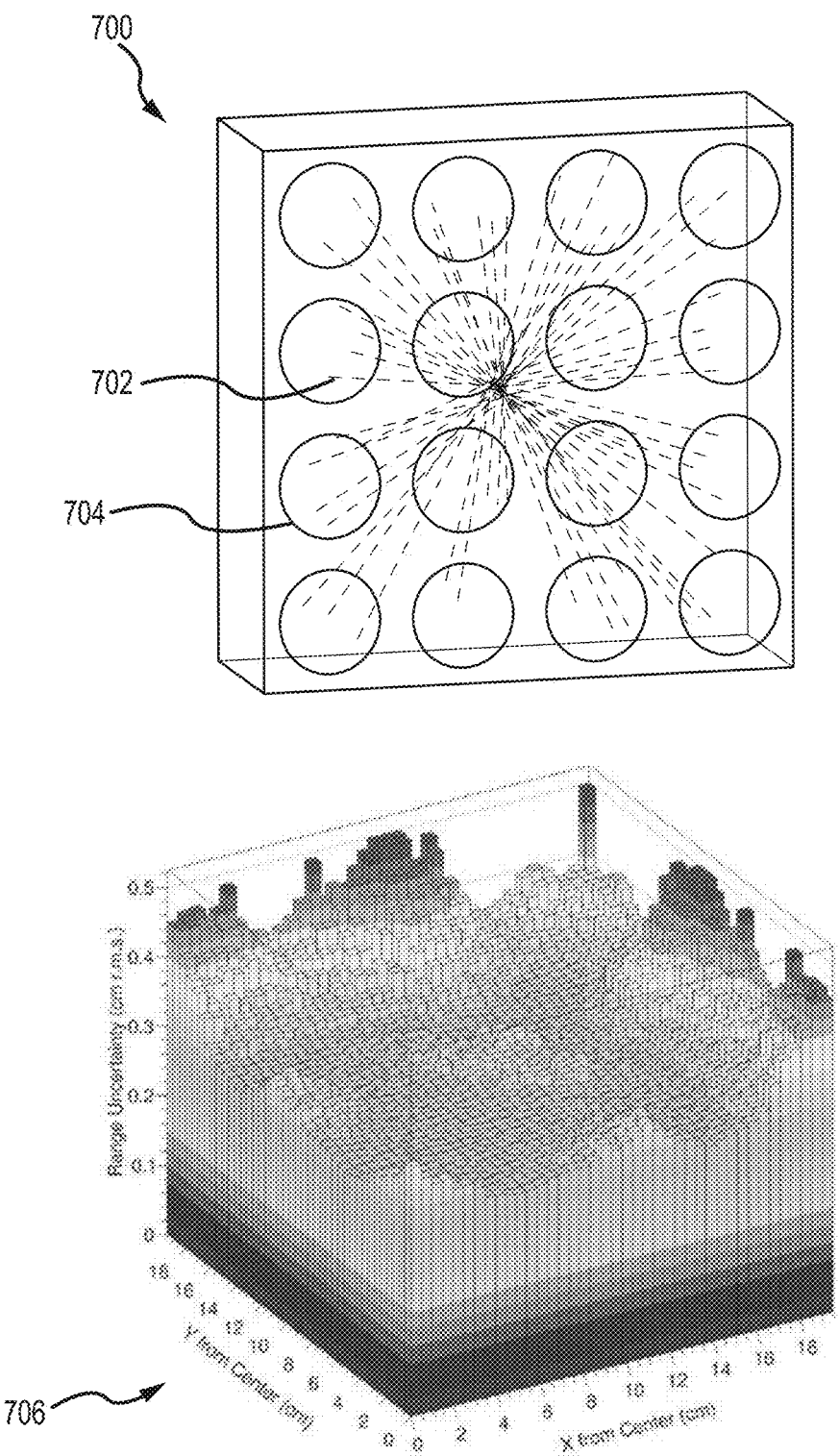
FIG. 7 shows a first detector placement simulation according to the disclosure.

FIG. 7 depicts residual range detector 700 and simulated generated photons 702 that are generated by a proton interacting with the scintillator material. Circles 704 depict the locations of photon detectors coupled to the scintillator material. The photon detectors capture a certain number of generated photons 702 and produced a corresponding electrical signal representative of the number of photons that were captured. The collection efficiency of residual range detector 700 varies based on the location that the proton entered the scintillator material. Lower collection efficiency may result in higher uncertainty in the residual range of a proton. For example, with respect to the uncertainty data in graph 706, which represents data for a quadrant of residual range detector 700, the collection efficiency at the edge of the scintillator material (further from the center along the x or y axis) is lower because the sides of scintillator material are anti-reflective. This results in a higher uncertainty for the residual range near the edges of residual range detector 700.

Graph 706 also shows that higher uncertain may occur when a proton enters scintillator material in between where the photon detectors are coupled to the scintillator material.

FIG. 8 depicts residual range detector 800 and simulated generated photons 802 with a different configuration of photon detectors (not shown). As can be seen by the locations of circles 804 that represent the locations where photon detectors are coupled to the scintillator material, the photon detectors in residual range detector 800 are spaced closer together than in residual range detector 700 of FIG. 7. As can be seen in the residual range uncertainty in graph 806, the closely spaced photon detectors in residual range detector 800 can determine the residual range of protons that enter the center of residual range detector 800 with less and more uniform uncertainty as compared to residual range detector 700 of FIG. 7. The uncertainty at the edge of residual range detector 800, however, is higher than the uncertainty at the edge of residual range detector 700 of FIG. 7.

The differences in performance between residual range detectors 700 and 700 of FIGS. 7 and 8, respectively, show that a residual range detector can be configured according to advantageous specifications. For high accuracy and large detection fields, a large number of closely spaced photon detectors may be needed. If, however, slightly lower accuracy is acceptable, a lower number of more widely spaced photon detectors could be used to reduce cost and complexity.

Figure 9:
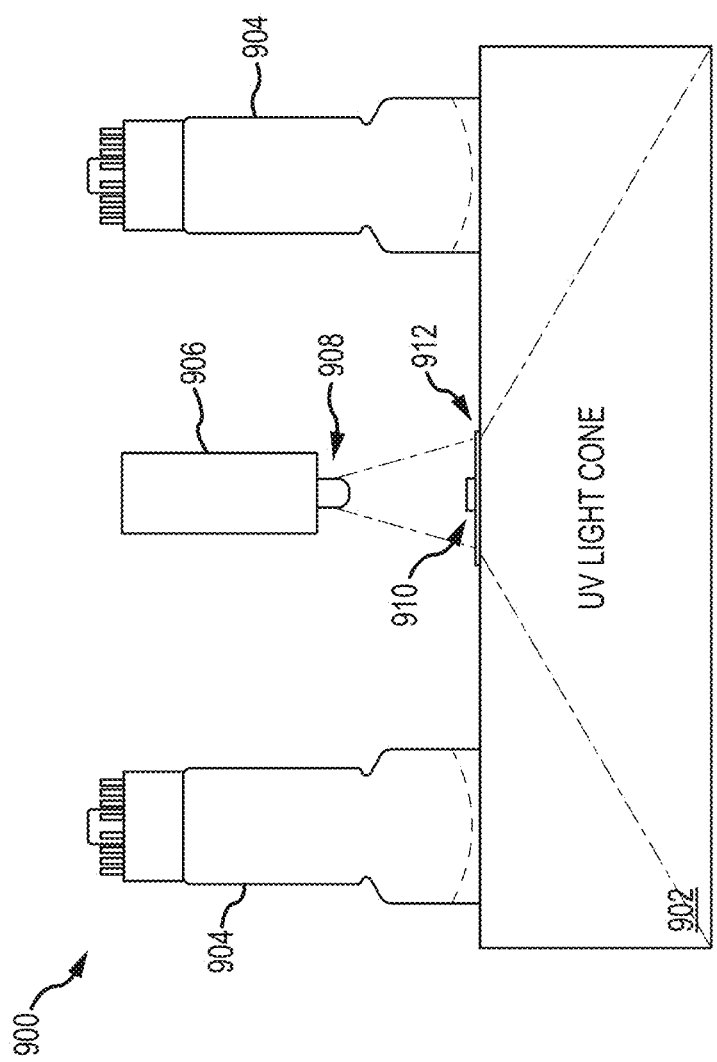
FIG. 9 shows a detector gain calibration system according to the disclosure.

FIG. 9 shows a detector gain calibration system 900 that, in some examples, is used to calibrate a residual range detector (such as residual range detector 110 of system 100 in FIGS. 1 and 2) having scintillator material 902 and photon detectors 904. Calibration system also includes pulse generator 906, UV LED 908, photodiode 910, and diffuser 912. In other example calibration systems, a diffuser may not be used.

In one example, in a residual range detector that uses a 4×4 array of photon detectors, such as photomultiplier tubes (PMT), each PMT is labeled PMT_ij where i and j and the row and column of each PMT. Using analog summing electronics, we form three output signals from sixteen input signals. This allows three channels to be digitized channels instead of sixteen, which is a major savings in cost of electronics and data volume. The three output signals are a total energy signal E, and two position dependent signals for diagonal coordinates (rather than row-column coordinates).
  1. E, the sum of the sixteen PMT signals.
  2. U, 3*PMT_03+2*PMT_12+ . . . −3*PMT_30
  3. V, 3*PMT_00+ . . . −3*PMT_33
  4. Optionally, C, the sum of the central PMTs: C=PMT_12+21+11+22. This output signal may be used if, for example, the digitizer channels came in pairs and an extra channel is available.

The procedure to reconstruct proton residual range involves a two-step process:

The first step is to set and maintain the gains of the individual PMTs relative to a photodiode with LED pulsing, as shown in FIG. 9. A photodiode provides a convenient reference with stable unity gain, as long as care is taken to ensure temperature and gain stability of any preamplifiers. In some cases the PMTs gains are within approximately 25% of each other. This may cause a slight increase in the statistical error from the number of photons detected. The gains of the PMTs may be set and maintained individually to a value fixed relative to the photodiode.

Because the light collection efficiency of residual range detector 900 is position dependent (see discussion with respect to FIGS. 7 and 8), E may be corrected for the X and Y position of the proton track in scintillator material 902. Furthermore, there are fluctuations and correlations between E, U, and V for proton tracks at a particular position, and an optimal reconstruction may take these into account.

The second step is to acquire a calibration data set, organized with protons in a 3D grid: X, Y, and residual range R. In some examples, a grid spacing of 0.5 cm for all 3 coordinates is used. X and Y can be determined from the tracking system and events within approximately 0.5 mm from the center of each grid point may be selected. For each grid point, labeled by X, Y, and R, the average E, U, and V, as well as the 3D covariance matrix (optionally, C can be included for a 4D covariance matrix) may be saved as calibration data for use later.

For an individual proton with measured X, Y, E, U, V, the grid of data can be used to reconstruct the residual range. For a hypothesized residual range, the following steps may be used:
  1. Interpolate the average E, U, and V as well as the covariance matrices first to the measured X and Y of the track, and then to the hypothesized R.
  2. Form a chi-square using the measured E, U, and V
  3. Find the hypothesized R with the minimum chi-square.

Figure 10:
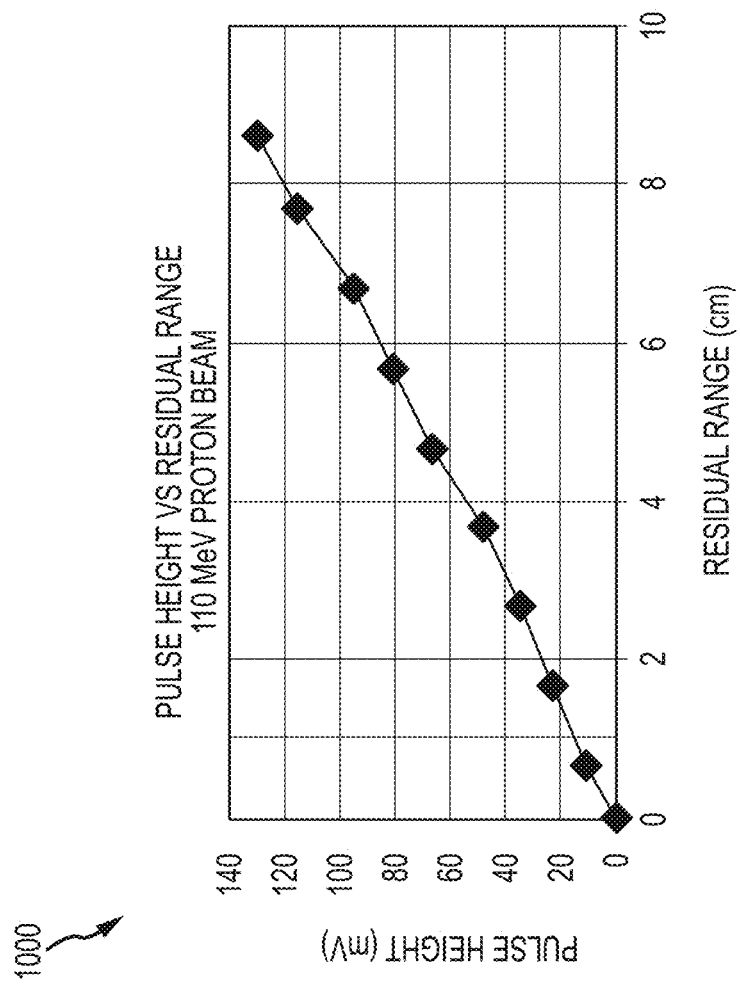
FIG. 10 shows a first experimental data set according to the disclosure.

FIG. 10 depicts experimental results in graph 1000 for a residual range detector according to the present technology (e.g., a residual range detector similar to residual range detector 110 of FIGS. 1 and 2). The pulse height measured in terms of mV shows an approximately linearly correlation with residual range of protons. The residual range detector that produced the results in graph 1000 included a 10×10×10 $cm^3$ active volume of plastic scintillator and a 2×2 array of PMTs.

Figure 11:
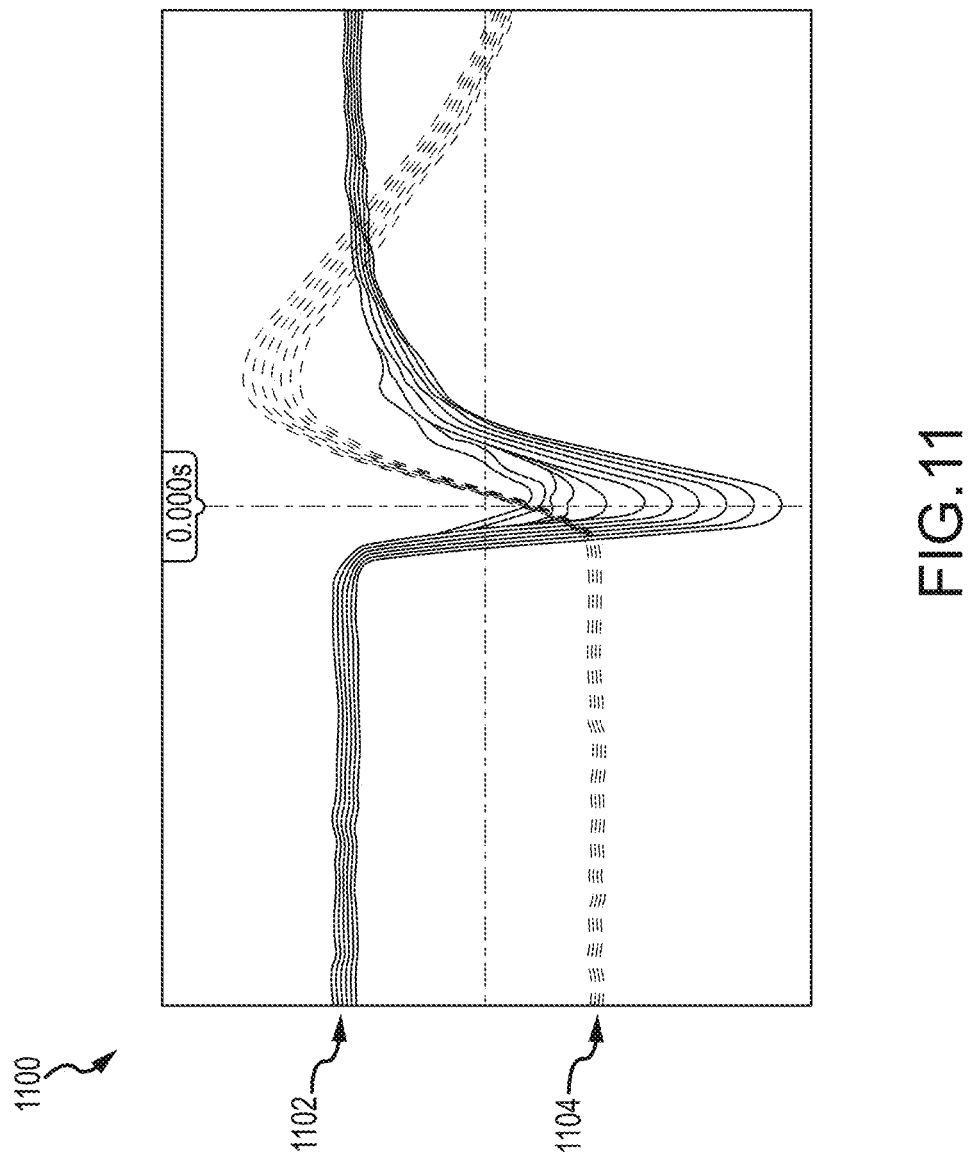
FIG. 11 shows a second experimental data set according to the disclosure.

FIG. 11 depicts graph 1100 containing data for spreads of pulse heights at one range setting of protons in the same experiment that produced the data of FIG. 11. Curves 1102 are signals from one PMT. Curves 1104 are the total energy signal.

Figure 12:
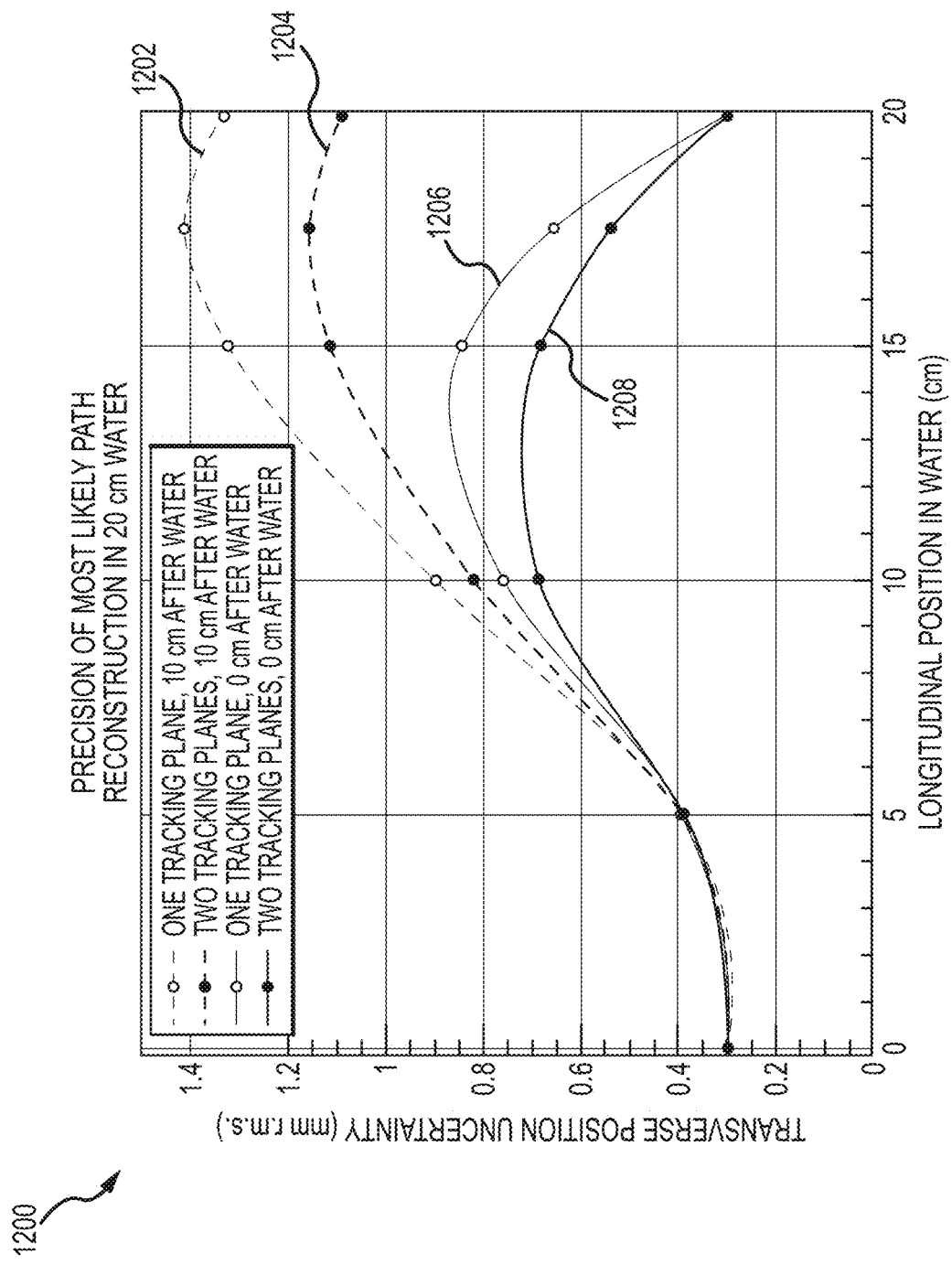
FIG. 12 shows a tracking plane or detector simulation according to the disclosure.
Figure 13:
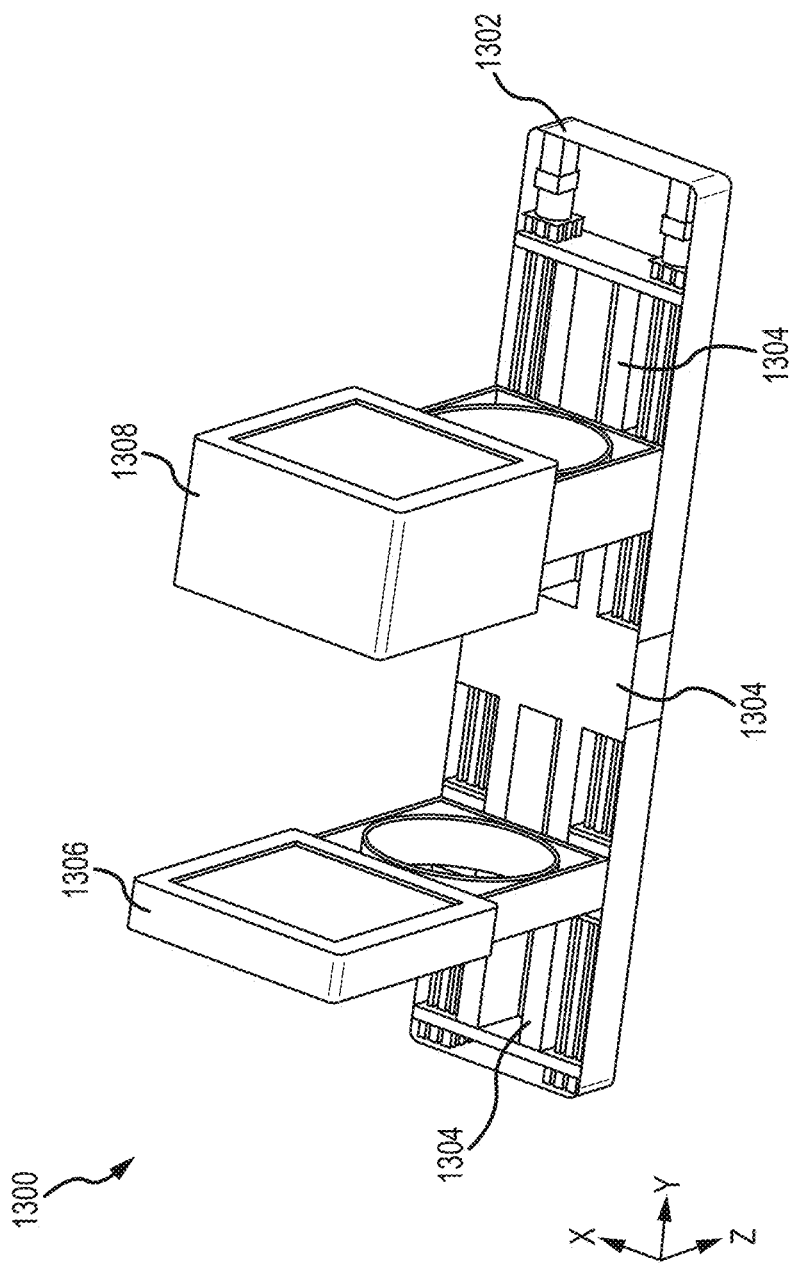
FIG. 13 shows a first position adjustment apparatus according to the disclosure.

FIG. 12 depicts graph 1200 of data for a tracking plane or detector simulation. Graph 1200 shows that using two tracking planes (tracking detector 106 would be considered "one" tracking plane) is better than using one, because transverse position uncertainty is lower (resolution is better) when two tracking detectors are used. Curve 1202 is for one tracking planes positioned 10 cm after water. Curve 1204 is for two tracking planes positioned 10 cm after water. Curve 1206 is for one tracking planes positioned 10 cm after water. Curve 1208 is for two tracking planes positioned 10 cm after water. As can be seen from graph 1200, there may be some benefit to using two tracking planes as opposed to one tracking plane. With respect to system 100 of FIG. 1, using two tracking planes may correspond, for example, to using two tracking detectors on one or both sides of object 104. In some cases when a pencil beam is used, only one tracking plane on the upstream side is necessary because the input direction is known as a function of detected proton position FIG. 13 depicts an example support structure 1300 that can be used to mount some components of system 100 of FIGS. 1 and 2. For example, support structure 1300 includes base 1302 and track 1304. Tracking detector 1306, which may correspond to tracking detector 106 of FIGS. 1 and 2, may be mounted on track 1304 so that tracking detector 1306 is moveable along base 1302. Tracking and residual range detector 1308 includes a tracking detector (such as tracking detector 108 of FIGS. 1 and 2) and a residual range detector (such as residual range detector 110 of FIGS. 1 and 2). Like tracking detector 1306, tracking and residual range detector 1308 is mounted on track 1304 so that tracking and residual range detector 1308 is moveable along base 1302. Tracking and residual range detector 1308 could also be separated into two distinct components.

Figure 14:
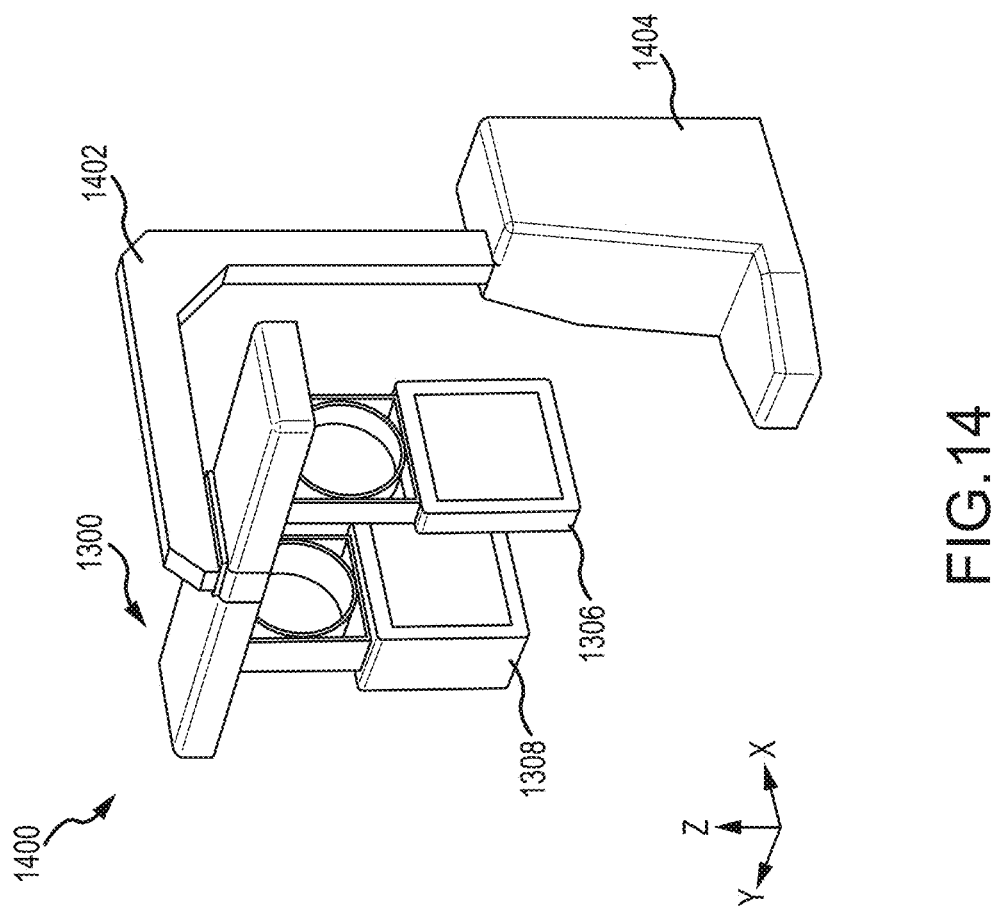
FIG. 14 shows a second position adjustment apparatus according to the disclosure.

FIG. 14 depicts mounting system 1400 for support structure 1300. Mounting system 1400 includes a mounting arm 1402 and a mounting base 1404. In some examples, mounting arm 1402 and/or mounting base 1404 is adjustable or controllable to position support structure 1300 into different positions as is helpful for treatment or imaging of an object between tracking detector 1306 and tracking and residual range detector 1308. Other example mounting systems can include the capability to rotate the angle at which an object is being imaged. With these system, some embodiments of the present technology can be used to implement tomography imaging systems that produce 3D data about the object.

Some embodiments of the disclosed detector of the present technology can transform the practice of proton radiation therapy because the same will enable facilities to efficiently and confidently deliver optimal treatments fully realizing the promise of the Bragg peak. As mentioned above, the Bragg peak enables particles such as protons or so-called heavy ions to precisely target tumors for radiation therapy while exposing healthy tissues to a smaller dose when compared with conventional radiation therapy. However, proton radiation therapy requires precise patient alignment and adjustment of proton initial energy, so that the proton beam has the correct range in the patient to stop in the tumor. In order to adjust the range of the proton beam, treatment planning uses a three-dimensional map of a patient in terms of relative stopping power, or the energy loss of protons of the beam in a material relative to that of water. Typically, such maps are obtained from x-ray computerized tomography scans; however, there are uncertainties or errors in converting x-ray absorption units (Hounsfield) to relative stopping power, and patient inhomogeneities introduce additional uncertainties. Furthermore, metallic implants or other high-density materials can cause shadowing artifacts and streaking.

Proton technology is not yet mature, and uncertainty margins are often greater than that for modern photon therapy. Thus, it is contemplated that there is a clear need to reduce alignment uncertainties, enable more complex treatments using more proton directions, deliver a higher dose to a tumor per treatment, and reduce range uncertainties such as to within 1.0 mm range precision. It is contemplated that such improvements, which use frequent imaging, should be accompanied by improvements in patient throughput to improve the cost-effectiveness of proton therapy relative to conventional radiation therapy. The significant expense of building and maintaining proton therapy facilities has been recognized as a major disadvantage, which has only recently been reduced by the development of more compact systems and single-room options. It is contemplated that new imaging technologies should integrate seamlessly into proton therapy systems to streamline and simplify patient operations, rather than add complexity and expense. The features or aspects of embodiments of the present technology may provide such and more benefits.

For example, the embodiments of the detector of the present technology may leverage at least one tracking detector to measure the transverse position of individual protons before and/or after a patient, and a residual range detector to determine the proton energy absorbed within the patient. Proton radiography produces two-dimensional images with a single projection angle, directly quantifying proton range through the patient rather than x-ray absorption power. Digitally reconstructed radiographs can be derived from previous x-ray computerized tomography scans and compared to proton radiographs to validate and improve relative stopping power maps and patient alignment. Proton computed tomography, by contrast, measures the three-dimensional relative stopping power map of a patient by acquiring many proton histories from many projection angles and applying advanced iterative reconstruction algorithms. While proton computed tomography may leverage the same or similar detector technology as proton radiography, proton computed tomography typically has greater operational complexity, produces larger data volumes, and uses proton energies high enough to traverse a patient in all directions. Additionally, the embodiment of the detector of the present technology may be leveraged to commercialize a proton radiography system producing two-dimensional images using protons with enough energy to traverse the patient. A subsequent radiation treatment uses a lower energy, higher intensity beam which terminates in a tumor. The use of a proton beam for both imaging and treatment streamlines patient setup and quality assurance procedures, reduces alignment uncertainties, and reduces range uncertainties.

Currently, radiation therapy is needed for more than 50% of the 1.6 million Americans who are annually diagnosed with cancer. A conservative estimate from the Mayo Clinic is that 137,000 new cancer patients each year in the United States could benefit from proton therapy, well above current capacity. Proton radiation therapy can potentially spare large amounts of normal tissue from low to intermediate radiation dose and avoid organs at risk. This reduces late effects and improves quality of life, and is especially important for patients with high cure rates and long survival times. A policy statement issued by the American Society of Therapeutic Radiation Oncology cites scientific evidence confirming that proton beam therapy is particularly useful in a number of pediatric patients, particularly those with brain tumors, as well as for certain adult cancers requiring high doses in close proximity to critical structures. Additional research on more common cancer disease sites, such as breast, prostate and lung, is ongoing, with clinical trials accruing patients in all three disease sites from proton therapy facilities in the United States. Currently, sixteen (16) proton therapy facilities with a total of fifty-six (56) treatment rooms are operating in the United States, with many more under development. The embodiment detector of the present technology has the potential to be adopted for routine use in all treatment rooms using pencil beam scanning, which is quickly becoming the standard, rather than broad beams individually tailored for each patient.

Some embodiments of the detector of the present technology are non-complex, lightweight, easily scaled to large field sizes, operates at high speed to avoid bottlenecks in patient throughput and exposes the patient to the minimum possible dose for a given resolution. Proton radiography is not currently used routinely due to designs that are bulky, expensive and difficult to incorporate into the clinical environment. It is contemplated that an alternative is to use a single detector plane behind the patient and vary the proton energy to find the range through the patient. However, drawbacks to this approach include for example: inefficient use of proton dose since most protons do not contribute to measurement; poor spatial resolution since protons are not tracked; and, by using a broad beam for imaging, does not use the same beam system as for treatment in the case of pencil beam scanning systems.

Some embodiments of the detector of the present technology leverage fast-scintillation detector technology and the high-performance design is non-complex and monolithic, thereby reducing construction costs. For example, a low channel count is leveraged to minimize electronics development costs, and residual range resolution of 3.0 mm per proton or better is achieved. At this level, the range resolution is dominated by intrinsic range fluctuations rather than detector measurements for typical patient dimensions. This is helpful in order to achieve the favorable dose performance of proton radiography, which averages measurements from many protons to form an image. Doses as low as 1.0 µGy (microgray) are possible for a resolution in Water Equivalent Path Length (WEPL) of 1.0 mm for each square pixel.

Some embodiments of the detector of the present technology enable measurement of up to 10 million protons per second, resolving individual protons as close as 10 nanoseconds. Accelerator systems deliver proton bunches at the frequency of their RF cavities, as illustrated in FIG. 3, with RF frequencies as high as 100 MHz. In the case of low-intensity beams for imaging, most bunches will be empty, and the remaining bunches will contain a single proton. A 10 MHz proton beam will have protons separated by an average of 100 nanoseconds, with a random separation distribution as close as 10 nanoseconds in time. As noted above in connection with FIG. 3, a small fraction of bunches will have two or more protons. These may be rejected for analyses but will still contribute to the dose. Advantageously, such speeds allow for, as an example, a 20×20 cm$^2$ field to be imaged with less than a second of beam time with a resolution in WEPL of 1 mm for each square pixel.

Some embodiments of the detector of the present technology are especially advantageous for pencil beam scanning systems. Pencil beams lead to protons sequentially hitting the same region of a detector, adding to the challenge of achieving high event rate capability. Further, use of pencil beams for both imaging and treatment will be very powerful for alignment and quality assurance, compared to imaging with a broad beam for example. Further, pencil beam position setting information can add redundancy to the position reconstruction, which is helpful for rejecting events with nuclear scatters or other problems. Further, a pencil beam scanning system can be used to divide the field for a proton radiograph into regions with different proton energy settings for each region based on the estimated range in that region, as obtained from a previous x-ray computerized tomography scan. This allows the system to maintain a low residual range for the protons as the beam scans across the patient, and has several benefits including for example: the residual range detector can be thinner, such as 10.0 cm or less, saving on weight and volume in the treatment area, and making the read-out easier; the lower total range for the protons is more optimal for range resolution relative to dose, lower range also results in fewer protons lost to nuclear interactions, which also results in lower dose for a given image quality.

Some embodiments of the detector of the present technology enable transverse position resolution, or "hit" resolution, of 0.3 mm or better in the disclosed tracking detectors. The continuous multiple scattering of a proton in matter limits spatial resolution. Measuring the proton transverse position before and after the patient can enable a typical uncertainty on the path through the patient as a function of depth of 0.5 mm, setting criterion for the hit resolution. Multiple scattering is more probable for lower energy protons, so a strategy of using lower energy protons to limit the residual range, while optimal for range resolution and practicality, has a potential drawback on spatial resolution. While range resolution is typically priority, a work-around for patients needing extra spatial detail would be to use a higher energy beam with additional passive material in front of the range detector. Resolution and dose trade-off would then be similar as for standard approaches.

In some examples, the residual range detector of the present disclosure comprises a rectangular volume of scintillator, with an array of large-area photomultiplier tubes mounted on the side downstream of the proton beam. The protons stop in the scintillator, generating a large number of scintillation photons within a few nanoseconds. To obtain fast signals, the sides not occupied by photomultiplier tubes are painted or covered with an anti-reflective material to absorb photons, and the photomultiplier tubes collect only direct photons that have not scattered off the walls. It is contemplated that signals from the photomultiplier tubes can be summed to produce a total energy signal, as well as weighted to produce an X-position signal and a Y-position signal. And, by recording only three signals per event (total energy, X-position, Y-position), a major advantage in electronics cost and data volume is achieved or realized. The high speed of the direct photon collection is another major advantage, compared to conventional designs with reflective surfaces that take much more time to collect the scintillation light and ultimately introduce errors in map reconstructions due to non-linearity in pulse height versus residual range trends. The monolithic design, combined with a strategy of limiting the residual range of the measurement, has the major advantages of reducing weight and optimizing dose. As an extra benefit, a position measurement is obtained from the residual range detector, adding extra redundancy useful for rejecting events with problems such as inelastic scatters.

Results have been obtained, as illustrated in at least FIGS. 10-11, with a residual range detector consisting of a 10×10×10 cm$^3$ active volume of plastic scintillator and a 2×2 array of photomultiplier tubes, and a pencil beam. The dependence of pulse height of the total energy signal on residual range is a consequence of the convolution of photon production and collection efficiency, and is approximately linear. The narrow spread in pulse heights at each range setting indicates that range resolution goals have been achieved. Additionally, as illustrated in at least FIG. 5, a pulsed light emitting diode may be used for photomultiplier tube gain calibration. Such a technique may be used to maintain constant gains by comparing to a very stable photodiode.

The tracking system of the present disclosure, as illustrated in at least FIG. 4, is based on scintillating fibers and multi-anode photomultiplier tubes. In some embodiments, 1.0 mm$^2$ fibers are used, with two layers each for X and Y coordinates. Adjacent fibers in different layers are bundled into single photomultiplier channels, and protons may be detected in as few as one channel per view. Along with some backing material, the total width of each tracking plane or detector may be about 0.5 cm, and may provide a typical hit resolution of about 0.3 mm. A field size of 38.4×38.4 cm$^2$ may allow entire field coverage with no gaps. Other examples are possible, and each example may be implementation-specific.

Using pencil beams and a position-sensitive range detector as disclosed allows for a reduction by a factor of twelve (12) the number of light sensors and electronics channels relative to conventional designs, by segmenting the tracker laterally, in orthogonal directions for X and Y, into strips 3.2 cm in width for example. Fibers are bundled, from the same position within different strips, into single photomultiplier tube anodes. The tracking system will precisely measure position within a strip, and information from the pencil beam settings or the proton radiograph will then indicate which strip the proton was in. In some embodiments, the total number of channels for a single X-Y tracking plane may be sixty-four (64) channels, and can be read out with a single multi-anode photomultiplier tube. Only the channels that are hit for a given event need to be recorded, based on a threshold detection algorithm. Pulse width may be approximately 10 nanoseconds. In comparison, for a 10 MHz pencil beam, the average time between hits for a fiber in the beam will be about 1000 nanoseconds. Therefore, a low overlap probability is achieved.

Thickness of tracking planes in terms of WEPL is a tradeoff, a worthwhile trade-off for the non-complex, fast system of the present disclosure which is scalable to large field sizes with no gaps between scintillating fibers. The trade-off involves a slightly higher dose for a given resolution: the relative dose increase is approximately the same as the relative material increase including the object to be imaged. For example, an extra 1 cm of tracking material will increase the dose to image a 20 cm object by 5%. It may be possible to gain 2% or 3% with a more optimized design in the future. However, much larger gains are possible by optimizing the strategy for the residual range measurement as described above.

Some embodiments of the detector of the present technology are leveraged at average proton rates up to 10 MHz, and measurements of ranges and positions of protons separated in time by as little as 20 nanoseconds or less. It is contemplated that if the detector cannot resolve events in adjacent bunches, these events will have to be discarded, slightly increasing the dose for a given image quality. Additionally, it is contemplated that the gain of the photomultiplier tubes should be high enough to obtain good signal-to-noise for low-range events, but low enough to remain within the current limits of the photomultiplier tubes for high-range (large pulse-height) events, especially when operating at 10 MHz.

Some embodiments of the detector of the present technology are leveraged to demonstrate resolution per proton in WEPL of 3.0 mm or better across the sensitive detector area. This is a key specification to optimize proton range resolution relative to dose to the patient. A worse resolution will still be functional but will result in increased dose to the patient. An image will average many proton measurements to obtain a resolution of 1 mm or better. Stable photomultiplier gains may be important to achieve such resolution. Frequent and efficient calibration strategies, and alternative photomultiplier tube choices, may be considered.

Embodiments of the detector of the present technology may be leveraged to demonstrate proton detection efficiency of greater than 97% per tracking plane, with transverse position resolution of 0.3 mm in order to maintain good spatial resolution. Undetected protons increase the dose without improving the image resolution. If the detection efficiency is not high enough, light yield may be increased through design. Alternatives include: using thicker scintillating fibers, with the drawback of adding additional material to the tracking detector(s); silicon photomultiplier sensors with large area are accessible, and may be an alternative to multi-anode photomultiplier tubes, with higher quantum efficiency.

Regarding calibration, LED pulsing maintains photomultiplier tube gains relative to a photodiode. Since photodiodes are very stable, with gain of 1.0, the concept in FIG. 7 is very effective. Proton beam data is then used to calibrate the total energy signal, the x-position signal, and the y-position signal. Calibration data may be acquired in a three-dimensional grid of transverse position across the field and proton residual range. The data can be binned in a dimensional grid with coordinates of measured total energy signal, x-position signal, and y-position signal. For each bin, the average true energy, x-position, and y-position are stored. For any event, the dimensional grid can be used as a look-up table, interpolating if helpful, the true quantities from the measured quantities.

Regarding performance of the residual range detector of the present disclosure, range stacks intrinsically add to range straggling in a measurement since the measurement is of the stopping point of the proton. Similarly, a segmented calorimeter adds to range straggling from the material in segments before the segment in which the proton stops. The monolithic design of the residual range detector of the present disclosure, combined with a strategy of limiting the residual range of the measurement, has a number of advantages such as the possibility of the residual range measurement being limited by the range straggling when the proton exits the patient, rather than by the material of the range detector itself. Since delivered dose decreases as the square as the range resolution improves, this may have a significant impact. Also, limiting the residual range reduces the fraction of protons lost to nuclear scatters, again improving the dose performance. And, as an extra benefit, a position measurement in the residual range detector is obtained, adding extra redundancy useful for rejecting nuclear scatters for example.

Regarding proton radiography versus proton computerized tomography, proton radiography checks the range through the patient, while proton computerized tomography potentially measures directly the range to the tumor. Proton computerized tomography uses much more data, beam time, analysis, operational complexity, and a patient thin enough for imaging from all directions. Through conversations with clinicians, it is found that a practical range check would be very useful and is a higher priority than longer-term proton computerized tomography development. A strategy for proton radiography may include for example: continue to rely on an x-ray computerized tomography scan for treatment planning; for each planned field, prepare in advance simulations showing the expected proton radiograph from that direction compare to the actual proton radiograph for alignment and range check; if desired, range checks from additional directions in addition to the treatment direction can be done; if the patient is too thick in the treatment direction, a range check and alignment may be possible from another direction; if the patient is too thick from all directions, an alignment check is still possible using the edges of the patient; if the range check passes, an error in the range to the tumor would have to involve an unexpected cancellation, with extra material in front of the tumor matched by a deficit behind the tumor.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory computer-readable medium such as a non-transitory storage medium. In some examples, one or more processors perform the described tasks.

Furthermore, the example embodiments described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A medical imaging system, comprising:
   a first tracking detector and a second tracking detector, wherein the first tracking detector is spaced from the second tracking detector to allow for an object to be present between the first tracking detector and the second tracking detector,
   wherein the first tracking detector includes first scintillating fibers and second scintillating fibers, wherein the first scintillating fibers extend in a direction perpendicular to the second scintillating fibers;
   a residual range detector adjacent the first tracking detector, the residual range detector including:
      a monolithic scintillator material having a first surface, wherein the first surface is at least partially covered with an anti-reflection material, and wherein the first surface faces the first tracking detector; and
      at least two photon detectors coupled to the monolithic scintillator material at a second surface of the monolithic scintillator material, wherein the second surface is different than the first surface;
   a proton source, wherein the proton source is configured to produce a pencil beam, and wherein the proton source is configured to steer the pencil beam across the second tracking detector; and
   a light detector connected to the first tracking detector, wherein the first scintillating fibers are divided into a plurality of strips, wherein each of the plurality of strips includes a plurality of adjacent scintillating fibers, wherein each of the plurality of adjacent scintillating fibers has a position in each of the plurality of strips, wherein terminal ends from each scintillating fiber at a first position in each of the plurality of strips are bundled together, and wherein the bundled terminal ends of the scintillating fibers at the first position in each of the plurality of strips are connected to an input of the light detector.

2. The system of claim 1, wherein the first surface is configured to be opposite the second surface.

3. The system of claim 1, wherein the first scintillating fibers include a first layer of scintillating fibers and a second layer of scintillating fibers, wherein a terminal end of a first scintillating fiber of the first layer of scintillating fibers is bundled together with a terminal end of a second scintillating fiber of the second layer of scintillating fibers adjacent to the first scintillating fiber to form a fiber doublet, and wherein the bundled terminal ends of the first scintillating fiber and the second scintillating fiber of the fiber doublet are connected to the input of the light detector.

4. The system of claim 1, wherein the terminal ends of each scintillating fiber at the first position in each of the plurality of strips are also bundled with the terminal end of another scintillating fiber of the first scintillating fibers.

5. The system of claim 1, wherein the at least two photon detectors are photomultiplier tubes.

6. The system of claim 1, wherein the first tracking detector is connected to a support and the second tracking detector is connected to the support, wherein the support is configured to allow the space between the first tracking detector and the second tracking detector to be adjusted by changing a position of the first tracking detector or a position of the second tracking detector.

7. The system of claim 1, wherein the monolithic scintillator material has a thickness of 10 cm or less.

8. The system of claim 1, wherein the anti-reflection material comprises black paint.

9. A method for providing a medical imaging system, comprising:
   providing a first tracking detector and a second tracking detector, wherein the first tracking detector is spaced from the second tracking detector to allow for an object to be present between the first tracking detector and the second tracking detector,
   wherein the first tracking detector includes first scintillating fibers and second scintillating fibers, wherein the first scintillating fibers extend in a direction perpendicular to the second scintillating fibers;
   providing a residual range detector adjacent the first tracking detector, the residual range detector including:
      a monolithic scintillator material having a first surface, wherein the first surface is at least partially covered with an anti-reflection material, and wherein the first surface faces the first tracking detector; and
      at least two photon detectors coupled to the monolithic scintillator material at a second surface of the monolithic scintillator material, wherein the second surface is different than the first surface;
   providing a proton source, wherein the proton source is configured to produce a pencil beam, and wherein the proton source is configured to steer the pencil beam across the second tracking detector; and
   providing a light detector, the light detector connected to the first tracking detector, wherein the first scintillating fibers are divided into a plurality of strips, wherein each of the plurality of strips includes a plurality of adjacent scintillating fibers, wherein each of the plurality of adjacent scintillating fibers has a position in each of the plurality of strips, wherein terminal ends from each scintillating fiber at a first position in each of the plurality of strips are bundled together, and wherein the bundled terminal ends of the scintillating fibers at the first position in each of the plurality of strips are connected to an input of the light detector.

10. The method of claim 9, wherein the first surface is configured to be opposite the second surface.

11. The method of claim 9, wherein the monolithic scintillator material has a thickness of 10 cm or less.

12. The method of claim 9, wherein the anti-reflection material comprises black paint.

13. The method of claim 9, wherein the at least two photon detectors are photomultiplier tubes.

14. A medical imaging system, comprising:
a first tracking detector and a second tracking detector, wherein the first tracking detector is spaced from the second tracking detector to allow for an object to be present between the first tracking detector and the second tracking detector,
wherein the first tracking detector includes first scintillating fibers and second scintillating fibers, wherein the first scintillating fibers extend in a direction perpendicular to the second scintillating fibers;
a residual range detector adjacent the first tracking detector, the residual range detector including:
a monolithic scintillator material having a first surface, wherein the first surface is at least partially covered with an anti-reflection material, and wherein the first surface faces the first tracking detector; and
at least four photomultiplier tubes coupled to the monolithic scintillator material at a second surface of the monolithic scintillator material, wherein the second surface is different than the first surface;
a proton source, wherein the proton source is configured to produce a pencil beam, and wherein the proton source is configured to steer the pencil beam across the second tracking detector; and
a light detector connected to the first tracking detector, wherein the first scintillating fibers are divided into a plurality of strips, wherein each of the plurality of strips includes a plurality of adjacent scintillating fibers, wherein each of the plurality of adjacent scintillating fibers has a position in each of the plurality of strips, wherein terminal ends from each scintillating fiber at a first position in each of the plurality of strips are bundled together, and wherein the bundled terminal ends of the scintillating fibers at the first position in each of the plurality of strips are connected to an input of the light detector.

15. The system of claim 14, wherein the first surface is configured to be opposite the second surface.

16. The system of claim 14, wherein the monolithic scintillator material has a thickness of 10 cm or less.

17. The system of claim 14, wherein the anti-reflection material comprises black paint.

* * * * *